United States Patent
Syeda-Mahmood et al.

(10) Patent No.: US 10,910,098 B2
(45) Date of Patent: Feb. 2, 2021

(54) AUTOMATIC SUMMARIZATION OF MEDICAL IMAGING STUDIES

(71) Applicant: International Business Machines Corporation, Armonk, NY (US)

(72) Inventors: Tanveer F. Syeda-Mahmood, Cupertino, CA (US); Ehsan Dehghan Marvast, Palo Alto, CA (US); Satyananda Kashyap, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 84 days.

(21) Appl. No.: 16/215,742

(22) Filed: Dec. 11, 2018

(65) Prior Publication Data
US 2020/0185083 A1   Jun. 11, 2020

(51) Int. Cl.
| G16H 30/40 | (2018.01) |
| G16H 15/00 | (2018.01) |
| G06T 7/00  | (2017.01) |
| G06K 9/62  | (2006.01) |

(Continued)

(52) U.S. Cl.
CPC ........... *G16H 30/40* (2018.01); *G06K 9/4647* (2013.01); *G06K 9/6212* (2013.01); *G06K 9/6215* (2013.01); *G06K 9/6228* (2013.01); *G06T 7/0016* (2013.01); *G06T 7/11* (2017.01); *G16H 15/00* (2018.01); *G06K 2209/05* (2013.01); *G06T 2207/30241* (2013.01)

(58) Field of Classification Search
CPC .......... G16H 30/40; G16H 15/00; G06T 7/11; G06T 7/0016; G06T 2207/30241; G06K 9/4647; G06K 9/6212; G06K 9/6215; G06K 9/6228; G06K 2209/05
See application file for complete search history.

(56) References Cited

U.S. PATENT DOCUMENTS

| 8,014,576 B2 | 9/2011 | Collins et al. |
| 8,369,593 B2 | 2/2013 | Peng et al. |
| 8,391,574 B2 | 3/2013 | Collins et al. |

(Continued)

OTHER PUBLICATIONS

Kalinic, Hrvoje, "Atlas-based image segmentation: A Survey", Department of Electronic Systems and Information Processing, University of Zagreb, 2009, pp. 1-7.

(Continued)

*Primary Examiner* — Mia M Thomas
(74) *Attorney, Agent, or Firm* — Stephen J. Walder, Jr.; William J. Stock (57) ABSTRACT

Medical imaging study summary engine mechanisms are provided. The mechanisms receive a medical imaging study having data representing a plurality of medical images of a patient. The mechanisms generate a temporal trajectory data structure of at least a subset of the medical images in the plurality of medical images, wherein the temporal trajectory data structure specifies topological changes in temporally subsequent medical images in the plurality of medical images. The mechanisms select medical image data corresponding to selected medical images from the medical imaging study data structure based on the temporal trajectory data structure. The mechanisms output the selected medical image data via a medical imaging study user interface.

19 Claims, 5 Drawing Sheets
(1 of 5 Drawing Sheet(s) Filed in Color)

(51) Int. Cl.
*G06T 7/11* (2017.01)
*G06K 9/46* (2006.01)

(56) References Cited

U.S. PATENT DOCUMENTS

| | | | | |
|---|---|---|---|---|
| 8,589,400 | B2* | 11/2013 | Naeymi-Rad | G06Q 50/22 707/738 |
| 8,744,149 | B2* | 6/2014 | Nakamura | G16H 10/60 382/128 |
| 9,098,611 | B2* | 8/2015 | Pinter | H04N 7/185 |
| 9,313,623 | B1* | 4/2016 | Ledet | G06F 19/3456 |
| 9,717,439 | B2* | 8/2017 | Giftakis | A61B 5/0476 |
| 9,798,857 | B2 | 10/2017 | Arazi et al. | |
| 9,892,341 | B2 | 2/2018 | Reicher et al. | |
| 10,331,852 | B2 | 6/2019 | Dormer et al. | |
| 10,340,044 | B2 | 7/2019 | Yao et al. | |
| 10,360,999 | B2 | 7/2019 | Bernard et al. | |
| 10,362,935 | B2 | 7/2019 | Dastmalchi et al. | |
| 10,387,612 | B2 | 8/2019 | Wu et al. | |
| 10,445,462 | B2 | 10/2019 | Sorenson et al. | |
| 10,452,813 | B2 | 10/2019 | Sorenson et al. | |
| 10,460,508 | B2 | 10/2019 | Zhan et al. | |
| 10,468,128 | B2* | 11/2019 | Davies | G06F 3/04847 |
| 10,475,182 | B1 | 11/2019 | Chilamkurhy et al. | |
| 10,476,848 | B2 | 11/2019 | Westin et al. | |
| 10,490,309 | B1* | 11/2019 | McNair | G16H 40/67 |
| 10,503,774 | B2 | 12/2019 | Saalbach et al. | |
| 10,522,248 | B2 | 12/2019 | Beymer et al. | |
| 10,540,763 | B2 | 1/2020 | Reicher et al. | |
| 10,540,803 | B2 | 1/2020 | Westerhoff et al. | |
| 10,541,048 | B2 | 1/2020 | Zhang et al. | |
| 2004/0044546 | A1* | 3/2004 | Moore | G16H 50/20 705/2 |
| 2012/0250961 | A1* | 10/2012 | Iwasaki | G06F 19/321 382/128 |
| 2013/0083894 | A1* | 4/2013 | Niebler | A61B 6/4441 378/62 |
| 2014/0180715 | A1* | 6/2014 | Phillips | G16H 40/67 705/2 |
| 2015/0035959 | A1* | 2/2015 | Amble | A61B 8/13 348/74 |
| 2015/0228042 | A1* | 8/2015 | Gencarelli | G06F 19/00 705/2 |
| 2016/0088257 | A1* | 3/2016 | Kim | G06F 19/3418 348/14.07 |
| 2016/0206292 | A1* | 7/2016 | Vezina | A61B 8/469 |
| 2016/0283664 | A1* | 9/2016 | Tubman | G16H 10/60 |
| 2016/0328526 | A1* | 11/2016 | Park | G06N 20/00 |
| 2016/0345923 | A1* | 12/2016 | Wakai | A61B 6/504 |
| 2017/0053075 | A1* | 2/2017 | Moses | G06F 19/328 |
| 2017/0176208 | A1* | 6/2017 | Chung | H04N 5/23293 |
| 2018/0110475 | A1* | 4/2018 | Shaya | A61B 5/746 |
| 2018/0196922 | A1* | 7/2018 | Abuelsaad | G16H 50/30 |
| 2018/0292978 | A1* | 10/2018 | Davies | G06F 3/04845 |
| 2018/0301222 | A1* | 10/2018 | Dew, Sr. | G06Q 10/00 |
| 2019/0034494 | A1* | 1/2019 | Bradley | G06Q 10/0637 |
| 2019/0139642 | A1 | 5/2019 | Roberge et al. | |
| 2019/0198157 | A1* | 6/2019 | Beymer | G06K 9/00765 |
| 2019/0198158 | A1* | 6/2019 | Beymer | G16H 30/40 |
| 2019/0214118 | A1 | 7/2019 | Reicher | |
| 2019/0223725 | A1 | 7/2019 | Lu et al. | |
| 2019/0287660 | A1* | 9/2019 | Oliveira | G16H 40/63 |
| 2019/0371475 | A1* | 12/2019 | Oliveira | G16H 10/60 |
| 2019/0392942 | A1 | 12/2019 | Sorenson et al. | |
| 2020/0111546 | A1* | 4/2020 | Syeda-Mahmood | G16H 15/00 |

OTHER PUBLICATIONS

Mahmood, R. et al., "Automatic Detection of Left Ventricular Aneurysms in Echocardiograms", IEEE International Symposium on Biomedical Imaging (ISBI), Apr. 16-19, 2015, 4 pages.

* cited by examiner

AUTOMATIC SUMMARIZATION OF MEDICAL IMAGING STUDIES

BACKGROUND

The present application relates generally to an improved data processing apparatus and method and more specifically to mechanisms for performing automatic summarization of medical imaging studies.

In today's modern medical industry, medical imaging is an important technology to assist medical professionals in obtaining an understanding of the internal medical conditions of a patient. Medical imaging is the technique and process of creating visual representations of the interior of a body for clinical analysis and medical intervention, as well as visual representation of the function of organs or tissues. With the advent of computer based medical imaging, databases of anatomies and physiology have been compiled to assist with identifying abnormalities. Various imaging technologies have been developed and utilized including X-ray radiography, magnetic resonance imaging (MRI), medical ultrasonography (ultrasound), endoscopy, elastography, tactile imaging, thermography, medical photography, nuclear medicine functional imaging techniques, such as positron emission tomography (PET) and single-photon emission computed tomography (SPECT), and the like.

Medical imaging often involves performing a medical imaging study of the patient. The medical imaging study involves capturing a large number of medical images of the patient's anatomy and may include hundreds or even thousands of individual medical images. The medical images of the medical imaging study must then be reviewed manually by a trained medical imaging specialist, e.g., a radiologist, sonographer, or the like, to determine which, if any, of the medical images in the medical imaging study, show anomalies or regions of interest that should be further evaluated. Thus, while the capturing of medical images may be a semi-automated technology involving computer based medical imaging systems, the evaluation of the captured medical images is largely a manual process requiring trained experts in the particular medical imaging technology being utilized.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising a processor and a memory, the memory comprising instructions that are executed by the processor to configure the processor to implement a medical imaging study summary engine. The method comprises receiving, by the medical imaging study summary engine, a medical imaging study data structure having data representing a plurality of medical images of a patient. The method also comprises generating, by the medical imaging study summary engine, a temporal trajectory data structure of at least a subset of the medical images in the plurality of medical images, wherein the temporal trajectory data structure specifies topological changes in temporally subsequent medical images in the plurality of medical images. Moreover, the method comprises selecting, by the medical imaging study summary engine, medical image data corresponding to selected medical images from the medical imaging study data structure based on the temporal trajectory data structure. In addition, the method comprises outputting, by the medical imaging study summary engine, the selected medical image data via a medical imaging study user interface.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention, as well as a preferred mode of use and further objectives and advantages thereof, will best be understood by reference to the following detailed description of illustrative embodiments when read in conjunction with the accompanying drawings, wherein.

DETAILED DESCRIPTION

As mentioned above, medical imaging studies often result in large numbers of individual images being captured of a patient's internal anatomy, e.g., hundreds or thousands of medical images depending on the particular medical study being conducted. A radiologist, sonographer, or the like, must manually parse through the images to identify those images that are of particular interest to the particular goal of the study, such as those that identify anomalies or regions of interest to the particular study. This is a time consuming and manual process which may be prone to errors or overlooking important images buried within the medical imaging study. Moreover, the process is dependent upon the particular expertise of the human being performing the manual review of the medical images in the medical imaging study.

The illustrative embodiments provide a computerized tool for performing automatic summarization of medical imaging studies. The mechanisms of the illustrative embodiments operate on a medical imaging study, comprising a large number of digital medical images of one or more medical image capturing technologies, and selects salient images from the medical imaging study to include in a summary of the medical imaging study for presentation to a medical professional, medical imaging expert, or other authorized user. The selection of the salient images is based on region segmentation of the medical images, atlas image based region of interest selection, topological feature extraction, temporal feature trajectory extraction, scale-space analysis, peak detection, and key image selection based on the peak detection, as will be described in greater detail hereafter. The result is that the mechanisms of the illustrative embodiments select medical images from a medical imaging study based on a saliency measured using topological variations of anatomical regions. The summary generated by the illustrative embodiments comprises those selected medical images that show significant changes in appearance of anatomical regions and hence, are salient. The generated summary optimizes the workflow of medical professionals, medical imaging specialists, and other persons that may be tasked with evaluating medical images, by bringing salient images to their attention and reducing the number of medical images they have to study.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for generating a summary output of a medical imaging study by selecting salient images from the medical imaging study based on identified topological variations of anatomical regions. The selected subset of salient medical images are then composed into a storyboard representation of the medical imaging study that is presented to a medical professional, medical imaging specialist, or other authorized user as part of a graphical user interface depicting a summary of the medical imaging study. In this way, the user is presented with the most salient medical images from the medical imaging study in a condensed, easy to use, interface that brings their attention to the medical images showing the anatomical structures that are of most interest to the purpose for which the user is reviewing the images in the medical imaging study. This greatly improves the user's workflow by reducing the number of medical images that the user must review in order to obtain the information they need to make decisions regarding the medical condition of the patient and potential treatments for the patient.

Figure 1A:
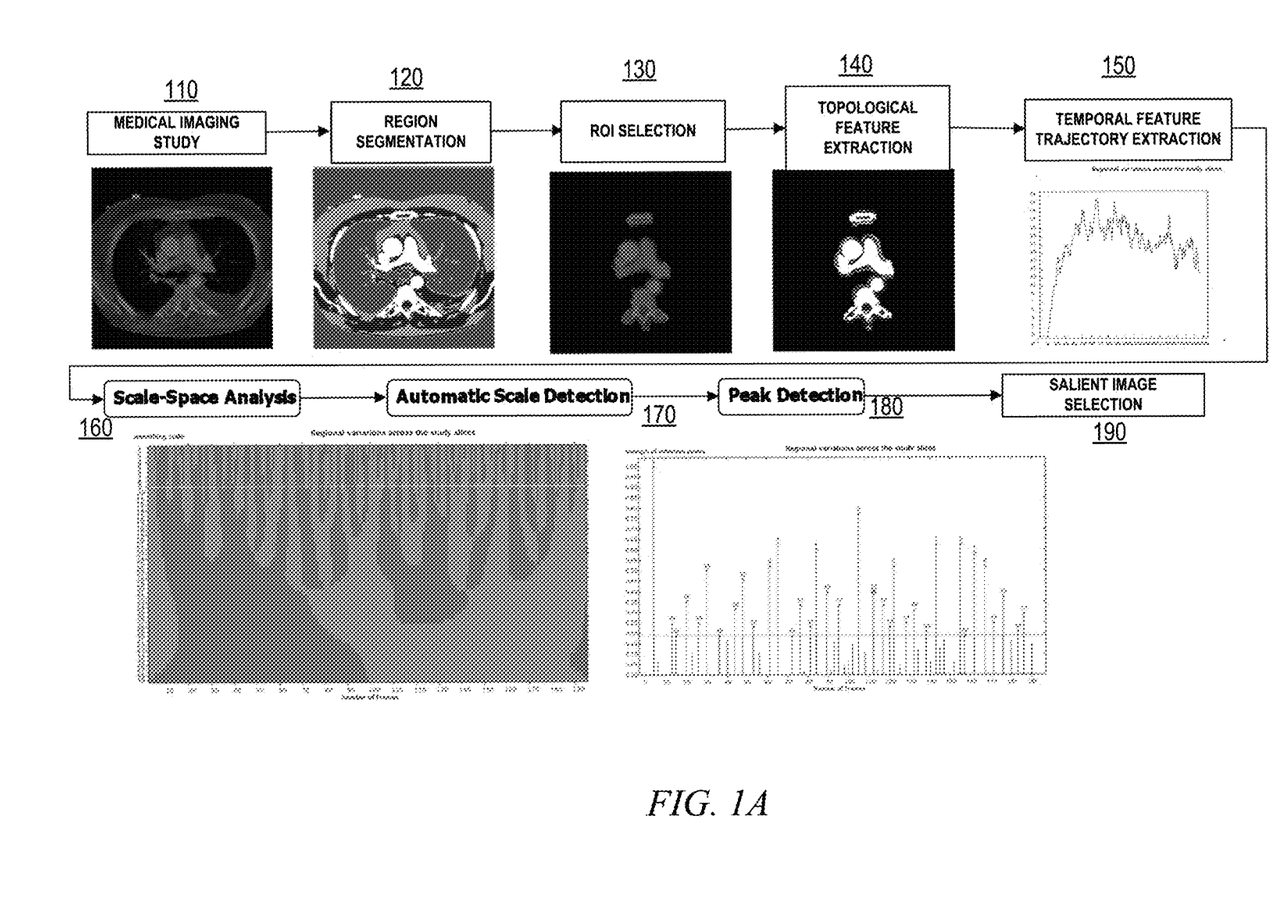
FIG. 1A is an example block diagram illustrating an outline of the operations for generating a medical imaging study summary in accordance with one illustrative embodiment.

FIG. 1A is an example block diagram illustrating an outline of the operations for generating a medical imaging study summary in accordance with one illustrative embodiment. As shown in FIG. 1A, with the mechanisms of the illustrative embodiments, given a medical imaging study 110, comprising a time series of captured medical images of a patient's anatomy (only one being shown in FIG. 1A for conciseness), obtained from medical imaging source equipment, computing systems, or the like, e.g., MRI, CT, X-ray, PET, or the like systems (not shown), each medical image in the series of images 110 is segmented using region segmentation 120 based on the intensity of pixels that correspond to various tissue types. Medical image segmentation is generally known in the art and involves the automatic or semi-automatic detection of boundaries of structures within a two or three dimensional medical image. Various algorithms and methodologies have been developed to perform such segmentation and identification of structures within a medical image. In some cases, such segmentation is based on an evaluation of pixel characteristics, e.g., intensity values, color values, etc. where sharp differences in such characteristics are indicative of boundaries of structures. The identified bounded structures may then be matched to labels corresponding to anatomical structures based on matching to a labeled set of medical images, manual labeling of the image, or the like. Any currently known, or later developed, methodology, algorithm, or computerized tool for performing medical image segmentation may be used with the mechanisms of the illustrative embodiments to perform the segmentation of the medical images in a medical imaging study without departing from the spirit and scope of the present invention.

Once segmented, a region of interest (ROI) is selected 130 based on the particular application for which the analysis of the medical imaging study is being performed. For example, when invoking the mechanisms of the illustrative embodiments, a user may submit a request to the medical imaging study summarization mechanisms that specifies the particular medical imaging study to be processed as well as the criteria for performing the summarization, which may include a specification of the purpose of the summarization, e.g., cardiac study evaluation, pulmonary study evaluation, etc. which may be correlated with particular regions of interest, e.g., the heart and its corresponding structures, the lungs and their corresponding structures, etc. The actual identification of the ROI in the segmented medical images may be based on a comparison of the segmented medical image to known labeled medical images, also referred to as atlases. The use of atlases for image segmentation and region of interest selection is described, for example, in Hrvoje Kalinic, "Atlas-based Image Segmentation: A Survey," Department of Electronic Systems and Information Processing, University of Zagreb, 2009.

For each medical image, topological features are extracted 140 from the medical image (or slice as it is sometimes referred to). Depending on the particular region of interest (ROI) selected, and the particular purpose for which the medical imaging study summary is being generated, different topological features may be extracted. In general, these topological features may include various measurements of the anatomical structures present within the region of interest, e.g., tissue width, thicknesses of walls of structures, distributions of sizes of the structures in the region of interest, dimensions of the shapes within the region of interest, or the like. The topological features may comprise one or many topological features which may present a basis for generating a one dimensional or multi-dimensional representation of the region of interest.

The topological features may be extracted by applying to the medical image data, one or more topological operators, which may be implemented as computer executable code, or specific sets of parameters for configuring computer executable code, for identifying particular topological features of interest. The topological operators can be applied after a rough segmentation of the image into regions. In medical imaging, there are a few major tissues of interest, such as blood, parenchyma, fat, air, and bone, which are characterized by different Hounsfield unit ranges, and which may be specified as parameters or elements of the computer executable code of the topological operators.

Since different imaging devices may offer different ranges, the intensity levels for various tissue structures may be estimated using information in the medical image alone using an algorithm such as multi-level thresholding algorithm, e.g., a multi-level Otsu threshold, as described in R. Mahmood et al., "Automatic Detection of Left Ventricular Aneurysms in Echocardiograms," 2013 IEEE ISBI Conference, 242-249, IEEE (2015). Using a multi-level thresholding approach, the intensity histogram of the medical image is segmented into levels optimally chosen based on the distribution of intensities in the medical image, e.g., a CT image. For example, the image intensities may be segmented into N optimal levels $\{t_1^*, t_2^*, \ldots t_N^*\}$ giving N+1 classes: $C_1$ for $[1 \ldots t_1]$, $C_2$ for $[t_{1+1}, \ldots, t_2]$, $\ldots$, $C_{N+1}$ for $[t_{N+1}, \ldots, L]$ where L is the maximum intensity level observed. The optimal thresholds $\{t_1^*, t_2^*, \ldots t_N^*\}$ are chosen by maximizing the inter-class variance $\sigma_B^2$:

$$\{t_1^*, t_2^*, \ldots t_N^*\} = \text{argmax} \{\sigma_B^N(t_1, t_2, \ldots t_N)\} \quad (1)$$

where $$\sigma_B^N = \sum_{k=1}^{N} \omega_k(\mu_k - \mu_T)^2, \omega_k = \sum_{i \in C_k} p_i, \text{ and } \mu_k = \sum_{i \in C_k} \frac{i * p_i}{\omega_k},$$

where $p_i$ is the probability of the gray level i in the image, $\mu_k$ is the class weighted mean, and $\mu_T$ is the overall mean.

As part of this pre-processing, in addition to a multi-level thresholding of the image, color connected component grouping may be used to provide indications of regions of interest. With color connected component grouping, when using certain medical imaging technology, structures having similar characteristics, e.g., density of tissue and the like, show up in the image with a similar coloring or gray-scale, intensity, and the like. Hence, the system of the illustrative embodiments looks for portions of the image that have similar coloring, intensities, or the like, and groups them together to represent similar structures. The result of this pre-processing using multi-level thresholding and color connected component grouping is a set of regions of interest for further filtering.

Once the regions are obtained, in accordance with one illustrative embodiment, the following topological features are extracted from each region: (a) first moment or area, (b) second moments describing orientation, (c) the number of regions adjacent to another region. A histogram is formed of the range of values for each of these parameters. The peaks in the histogram are identified and used to form the respective portion of the overall topological feature vector. By computing this multi-dimensional feature vector on each successive image of the sequence (CT, Echo, MRI), a time-varying curve is formed. The overall structure of this curve is analyzed using scale-space methods.

That is, the topological features, along each of the dimensions of topological features extracted, are plotted along a time scale to show how the topological features, and hence the anatomical structures, in the region of interest change over time in the medical imaging study. This leads to the creation of curves along one or more dimensions. This analysis can be done on the entire image or within a pre-specified region of interest. For example, if a chest CT atlas is available, and the focus of the disease of interest is in the cardiac region, only the cardiac atlas is overlaid and used to prune irrelevant regions in the computation of the topological feature generation and the histograms of regional features that give rise to the feature vector.

A scale space analysis algorithm is used 160 to automatically detect the proper scale for analysis of the trajectory 170. In image processing, scale-space theory is a framework for handling image structures at different scales, by representing an image as a one-parameter family of smoothed images (the scale-space representation) parametrized by the size of the smoothing kernel used for suppressing fine-scale structures. The main type of scale space is the linear (Gaussian) scale space, which has wide applicability as well as the attractive property of being possible to derive from a small set of scale-space axioms. The corresponding scale-space framework encompasses a theory for Gaussian derivative operators, which can be used as a basis for expressing a large class of visual operations for computerized systems that process visual information. This framework also allows visual operations to be made scale invariant, which is necessary for dealing with the size variations that may occur in image data, because real-world objects may be of different sizes and in addition the distance between the object and the camera may be unknown and may vary depending on the circumstances.

Assuming a Gaussian scale space operation, a multi-dimensional scale-space representation of the curve, e.g., the temporal trajectory curve of the illustrative embodiments, is denoted where C(t,σ) is the curve and G(t,σ) is the Gaussian curvature. Change points on the curve correspond to inflection points, i.e. places where there are zero-crossings of the second derivative. Salient change points are those that are preserved even after multiple levels of smoothing. In particular, by successively smoothing f(t) using a Gaussian of varying sigma, a smoothed curve C(t,σ) as:

$$C(t, \sigma) = C(t) * G(t, \sigma) = \int_{-\infty}^{\infty} C(u) \frac{1}{\sigma\sqrt{2\pi}} e^{\frac{-(t-u)^2}{2\sigma^2}} du \qquad (2)$$

If the scale σ is varied, the above smoothed signal is a 2D signal of time and σ. Since curvature change points are of interest, the extrema of slope or inflection points, i.e. points at which there is a zero-crossing in the second derivative, are identified as:

$$\frac{\partial C^2}{\partial t^2} = 0 \qquad (3)$$

To handle multi-dimensional signals, the derivative of the convolved multi-dimensional curve is generated and the magnitude of the change is recorded. The original inflection points can then be recovered from negative-going zero-crossings of the second derivative.

Although the scale-space theory is known, in the illustrative embodiments the image-rendered version of scale-space is utilized to interpret and identify salient change points. Specifically, in one illustrative embodiment, a two-dimensional (2D) image is formed from the scale-space curve with t on the horizontal access and \sigma on the vertical access. Choosing a level in this image corresponds to choosing a \sigma in the scale-space curve above. Each choice of sigma provides an increasingly smoother curve. The curvature change points in the curve are represented by the zero crossings of the negative derivative. The 2D image appears as shown by the red and blue image in FIG. 1A, where each zero-crossing of positive to negative value or vice versa is represented by the color change from red to blue. For a large curvature change, a large amount of smoothing is required for the curvature to disappear, thus such valley changes are seen at lower levels (corresponding to increasing sigma). Minor curvature changes disappear after a small amount of smoothing and are closer to the top of the image. Thus, by choosing a horizontal level in the image and retaining those valley changes that persist above this level, the salient curvature change points in the curve are identified. Choosing the horizontal cut off line, such as the one shown in white in FIG. 1A, may be performed by optimizing over two factors, namely, the level of smoothing desired, i.e. the total number of salient points to retain, and the approximation error for the curve shape by retaining only the salient points. This opposite growing curves of level of smoothing and approximation error intersect at an optimal point such as the one shown in FIG. 1A. The point at which they intersect is taken as the optimal scale. The peaks with their image valley peaks above the horizontal line are retained as the salient time points.

Since the salient time points are from the topological curve, they correspond to key medical images or frames in the imaging sequence. That is, the peaks in the trajectory indicate medical images in the medical imaging study where the topological features of the structures in the region of interest change significantly from one medical image to the next in the time series of medical images in the medical study. Thus, these are representative of medical images that are of interest to a user as part of the review of the medical imaging study, as they will typically represent the identification of anomalies in medical images.

Medical images corresponding to the peaks of the topological feature trajectory are selected as salient images 190, which are then used to generate a storyboard graphical user interface output in a summary of the medical imaging study which can be output to a medical professional, medical imaging specialist, or other authorized user via a graphical user interface on a computing system. That is, the peaks correspond to time points in the medical imaging study where a medical image was captured and thus, by correlating the time point with the timestamp of the medical image, the corresponding medical image from the medical imaging study may be selected as a salient medical image from the study. This can be done for each peak that is equal to or above a predetermined threshold along the selected scale, for example. Thus, through this process of processing a medical imaging study, a summary of the medical imaging study is generated that comprises a much smaller set of medical images that are determined to be the salient medical images of the medical imaging study most pertinent to the purpose for which the review of the medical imaging study is being conducted. As a result, the human user viewing the summary needs to review a substantially smaller set of medical images than he or she would otherwise have to in order to gather the information they need to perform an evaluation of the patient's medical condition and/or determine treatment options for the patient based on such medical conditions.

Figure 1B:
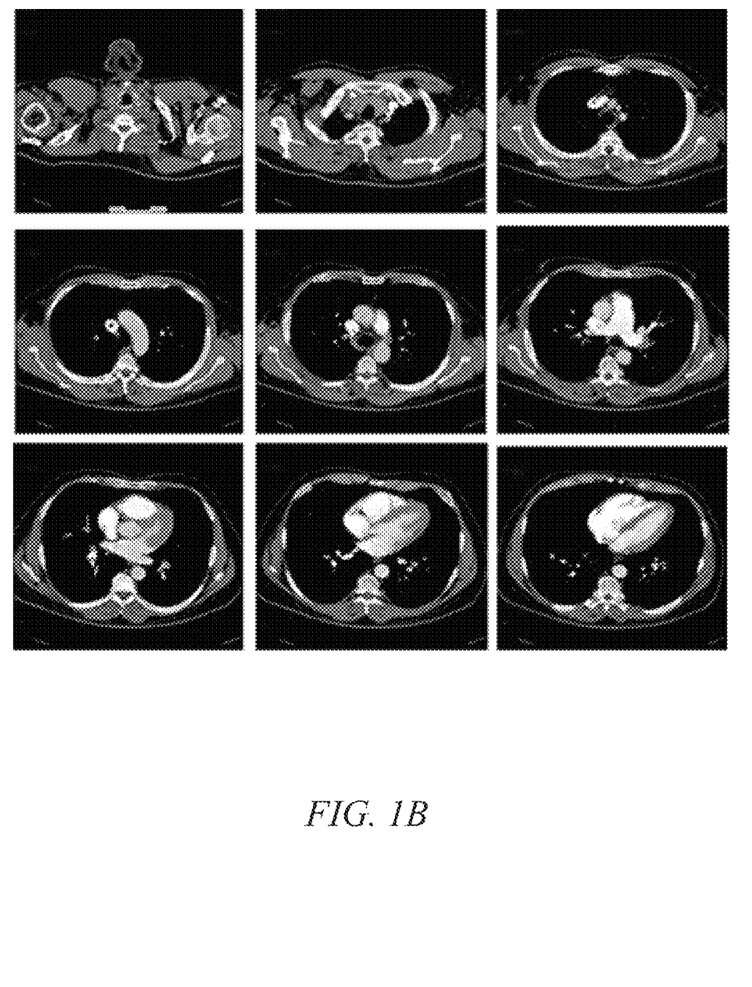
FIG. 1B is an example diagram illustrating a medical imaging study summary that is generated by the mechanisms of one illustrative embodiment.

FIG. 1B is an example diagram illustrating a medical imaging study storyboard output that may be generated using the mechanisms of the illustrative embodiments. FIG. 1B shows a storyboard that is generated by the mechanisms of the illustrative embodiments from a CT of over 182 medical images or frames. The resulting summary is compact but shows major anatomical structures at various levels in the body. Hence, rather than having to review 182 medical images, the user is presented with the most salient medical images of the medical imaging study for review, allowing the user to focus their efforts of diagnosing the patient and treating the patient on those images that are most relevant to the purposes of the medical imaging study and the medical conditions of interest. Moreover, by being able to focus the user's attention on the most salient medical images, the probability that the user may inadvertently overlook important medical images due to the large number of medical images present in the medical imaging study is lessened by operation of the medical imaging study summary generation computer tool of the present invention.

Figure 2:
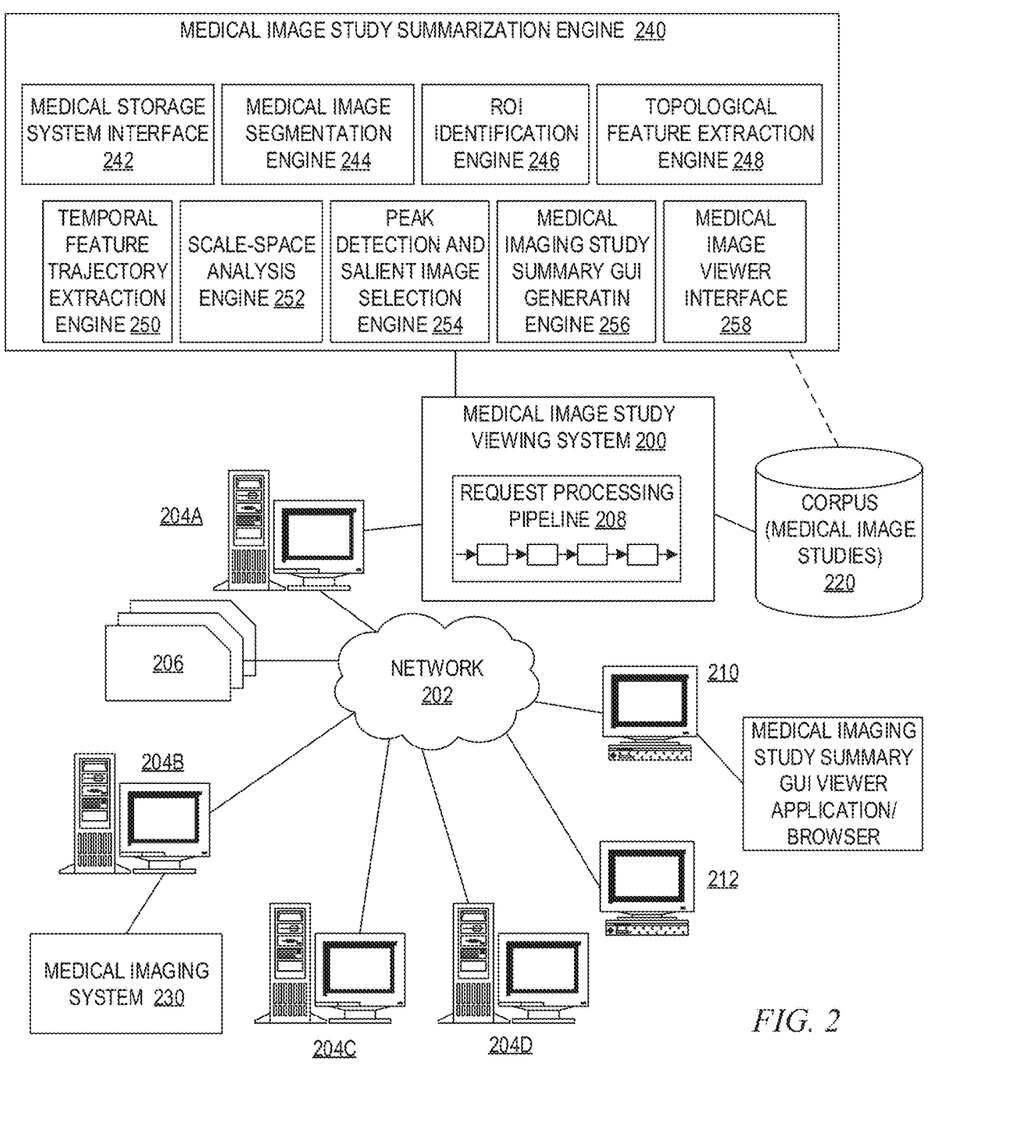
FIG. 2 is a schematic diagram of a medical image study viewing computing system in accordance with one illustrative embodiment.
Figure 3:
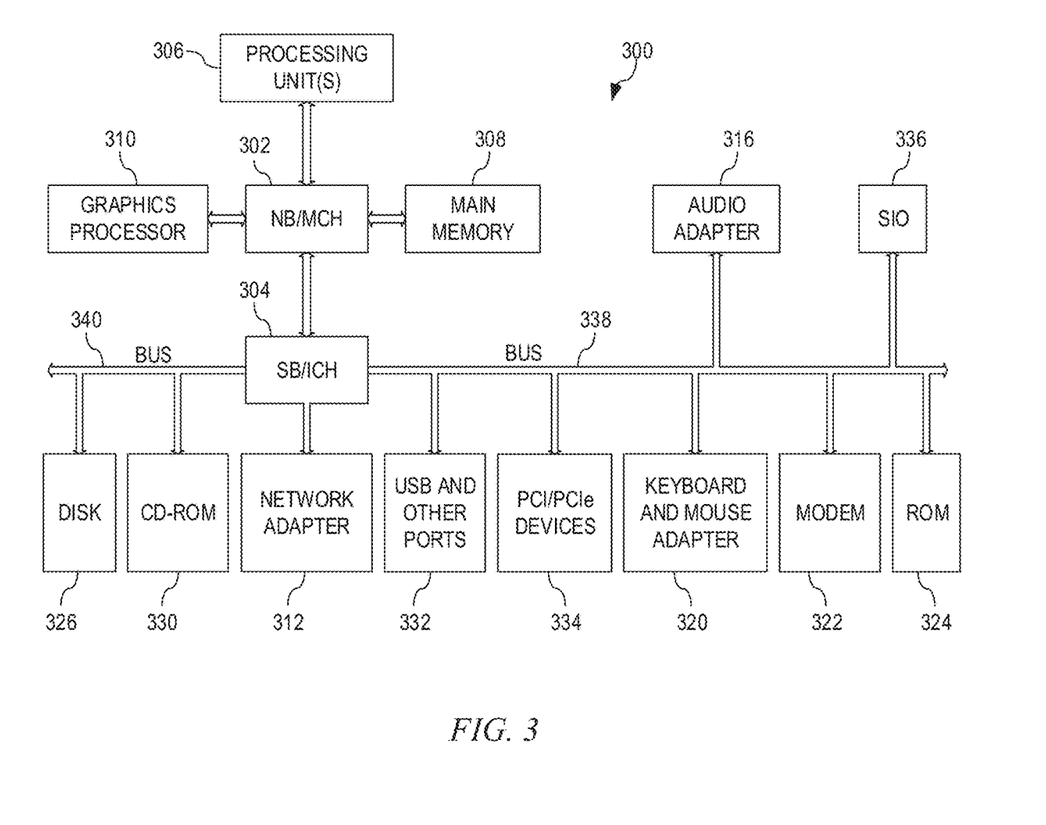
FIG. 3 is a block diagram of an example data processing system in which aspects of the illustrative embodiments are implemented.

It is clear from the above, that the illustrative embodiments are rooted in computer technology and define a new type of computing tool for generating and outputting summaries of medical imaging studies. Thus, it is apparent to those of ordinary skill in the art that the mechanisms of the illustrative embodiments may be implemented in various types of data processing environments as a computing tool. FIGS. 2 and 3 are examples of computing or data processing environments in which aspects of the illustrative embodiments may be implemented. It should be appreciated that FIGS. 2 and 3 are only examples and are not intended to assert or imply any limitation with regard to the environments in which aspects or embodiments of the present invention may be implemented. Many modifications to the depicted environments may be made without departing from the spirit and scope of the present invention.

FIG. 2 depicts a schematic diagram of one illustrative embodiment of a medical image study viewing computing system 200 implementing a request processing pipeline 208 in a computer network 202. The medical image study viewing computing system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the medical image study viewing computing system 100 being implemented on computing device 204A only, but as noted above the medical image study viewing computing system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like.

In some illustrative embodiments, the medical image study viewing computing system 200 and network 202 enables request processing functionality for one or more medical image study viewing computing system users via their respective computing devices 210-212. That is, a user may submit a request to the medical image study viewing computing system 200 via their client computing device 210, for example, to request viewing of a particular medical imaging study, which may be stored in a corpus in a storage system 206 which may be network attached, or a locally accessible storage system 220 that is locally accessible to the medical image study viewing computing system 200. The request may specify the particular medical imaging study to be viewed, e.g., patient identifier, date/time of the medical imaging study or other medical imaging study identifier, and one or more criteria for generating a medical imaging study summary, e.g., the purpose for the viewing, a designation of regions of interest for the summary, etc. The medical image study viewing computing system 200 may then operate on the request by processing the specified medical imaging study in accordance with an illustrative embodiment as described herein, to generate the medical imaging study summary output having salient medical images selected from the medical imaging study provided in a storyboard representation of a graphical user interface that is provided back to the requestor via the client computing device 210.

The medical image study viewing computing system 200 may be configured to implement a request processing pipeline 208 that receive inputs from various sources. The requests may be posed in the form of a natural language question, natural language request for information, natural language request for the performance of a cognitive operation, or the like. For example, the medical image study viewing computing system 200 receives input from the network 202, a corpus or corpora of documents or data structures 206, 220, cognitive system users, and/or other data and other possible sources of input. In one embodiment, some or all of the inputs to the medical image study viewing computing system 200 are routed through the network 202. The various computing devices 204A-D on the network 202 include access points for content creators and cognitive system users.

In some illustrative embodiments, these content creators may be medical imaging equipment or computing systems that utilize various medical imaging modalities to capture a time series of medical images of patient which are combined into a medical imaging study of the patient. For example, as shown in FIG. 2, the server 204B is associated with medical imaging system 230, which may be magnetic resonance imaging (MRI) system, computed tomography (CT) system, X-ray system, sonography system, positron emission tomography (PET) system, or the like.

The medical imaging system 230 provides medical images as data structures which are compiled into a larger data structure representing a time series collection of medical image data referred to as a medical imaging study data structure, which may be stored in one or more of the corpora 206, 220. Moreover, the one or more corpora 206, 220 may further comprise atlas medical images, and other supportive data structures that facilitate the operations of the illustrative embodiments as will be readily apparent to those of ordinary skill in the art in view of the present description.

In some illustrative embodiments, the computing devices 204A-D may include devices for a storing one or more databases representing the corpus or corpora of data 206, 220 (which are shown as a separate entities in FIG. 2 for illustrative purposes only). Portions of the corpus or corpora of data 206, 220 may also be provided on one or more other network attached storage devices, in one or more databases, or other computing devices not explicitly shown in FIG. 2. The network 202 includes local network connections and remote connections in various embodiments, such that the medical image study viewing computing system 200 may operate in environments of any size, including local and global, e.g., the Internet.

In one embodiment, the content creator, e.g., a medical imaging system 230, creates content in a document or data structure of the corpus or corpora of data 206, 220 for use as part of a corpus of data with the medical image study viewing computing system 200. The document or data structure includes any file, text, article, or source of data for use in the medical image study viewing computing system 200. Medical image study viewing computing system users access the medical image study viewing computing system 200 via a network connection or an Internet connection to the network 202, and input requests to the medical image study viewing computing system 200 that are processed based on the content in the corpus or corpora of data 206, 220.

In one embodiment, the requests are formed using natural language. The medical image study viewing computing system 200 may comprise natural language processing and/or cognitive processing engines which parse and interpret the request, and perform the corresponding operations for generating a requested output, which includes the operations of the illustrative embodiments to generate a medical imaging study summary output, via the pipeline 208. The results are provided as a response to the medical image study viewing computing system user that is transmitted to their client computing device, e.g., client computing device 110. The pipeline 208 implemented by the medical image study viewing computing system 200 may comprise a plurality of stages for processing an input request based on information obtained from the corpus or corpora of data 206, 220.

In some illustrative embodiments, the medical image study viewing computing system 200 may be implemented in conjunction with, or as part of, a cognitive system for healthcare applications (also referred to herein as a "healthcare cognitive system"). As such, the cognitive system may implement at least a portion of the request processing pipeline 208 as a Question Answering (QA) pipeline (also referred to as a Question/Answer pipeline or Question and Answer pipeline). The request processing pipeline 208 may be augmented to include logic stages for processing of queries generated from an input question or request using the medical image study summarization engine 240. For example, a user may submit a question to the cognitive system asking to be informed of the cardiac anomalies associated with patient P, i.e. "What are the cardiac anomalies for patient P?" As part of answering this question, the cognitive system may access patient electronic medical records, resource data structures, and the like, to perform a natural language text based analysis of such data structures from the corpus 206, 220, and in addition invoke the mechanisms of the illustrative embodiments to generate a medical imaging study summary to be output to the requestor as well, or on its own, that summarizes the medical imaging study for view by the requestor showing the salient images from the medical imaging study where anomalies are most likely depicted.

The requests input by users via their client devices 210-212 and network 202 to the cognitive system/medical image study viewing computing system 200 may be provided as structure or unstructured request messages, natural language questions, or any other suitable format for requesting an operation to be performed by the healthcare cognitive system and/or medical image study viewing computing system 200. As described herein, the particular healthcare application that is implemented in the cognitive system of the present invention is a healthcare application for medical imaging study summarization for decision support for a medical professional in which salient medical images are selected from the medical imaging study based on the identification of topological variations in anatomical structures present within a region of interest. The salient medical images are put together into a storyboard output that may be presented as part of a medical imaging study summary output graphical user interface for viewing by a user.

It should be appreciated that the healthcare cognitive system, while shown as having a single request processing pipeline in the examples herein, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained and/or configured to operate on input requests directed to processing the medical imaging study with regard to a first purpose and corresponding region of interest, e.g., cardiac evaluation, while another processing pipeline may be trained and/or configured to operate on input requests directed to processing the medical imaging study with regard to a second purpose and corresponding region of interest, e.g., pulmonary evaluation. As another example, different pipelines may be trained and/or configured to operate on different medical imaging modalities, views, and the like. The various pipelines may operate in parallel on the same medical imaging study and may generate different medical imaging study summaries based on their corresponding operations, each of which may be presentable to a user as a separate medical imaging study summary, or may be integrated into the same medical imaging study summary.

Moreover, each request processing pipeline may have their own associated corpus or corpora 206, 220 that they ingest and operate on, e.g., one corpus for medical images associated with the chest, another corpus for medical images of the brain, etc. These corpora may include atlases and other medical imaging resource data that may be used to support the operations of the cognitive system and the medical imaging study summarization engine of the illustrative embodiments. In some cases, the request processing pipelines may each operate on the same domain of input requests but may have different configurations, e.g., different annotators or differently trained annotators, such that different analysis and potential results are generated. The healthcare cognitive system may provide additional logic for routing input requests to the appropriate request processing pipeline, such as based on a determined domain of the input request, e.g., the purpose of the medical imaging study summarization, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. It should be appreciated that while some illustrative embodiments may be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What images show cardiac anomalies for patient P?", the cognitive system may instead receive a request of "Generate a cardiac anomaly medical imaging study summary for patient P," or the like. It should be appreciated that the mechanisms of the QA system pipeline, such as pipeline 208 for example, may operate on requests in a similar manner to that of input natural language questions with minor modifications. In fact, in some cases, a request may be converted to a natural language question for processing by the QA system pipelines if desired for the particular implementation.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

- Navigate the complexities of human language and understanding
- Ingest and process vast amounts of structured and unstructured data
- Generate and evaluate hypothesis
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language
- Deduce various language specific or agnostic attributes from natural language
- High degree of relevant recollection from data points (images, text, voice) (memorization and recall)
- Predict and sense with situational awareness that mimic human cognition based on experiences
- Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, medical imaging data, or other source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

The QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

Thus, in some illustrative embodiments, the medical image study viewing computing system 200 may be a separate independent computing system which provides functionality for viewing medical imaging studies and is augmented to include the mechanisms of the illustrative embodiments for generating medical imaging study summaries based on the identification of topological variations in anatomical structures across a time series of medical images in the medical imaging study. In other illustrative embodiments, the medical image study viewing computing system 200 may operate in conjunction with, or be integrated with, a cognitive system that is configured to provide healthcare cognitive operations, such as medical decision support functionality for medical personnel, such as doctors, nurses, technicians, and the like, to assist them in making determinations as to how to treat a patient. In these various illustrative embodiments, the computing systems are modified to include logic implemented in specialized hardware, specialized software executed on hardware, or any combination of specialized hardware and software executed on hardware, for implementing the medical imaging study summarization engine 240.

As shown in FIG. 2, the medical imaging study summarization engine 240 comprises a medical image storage system interface 242, a medical image segmentation engine 244, a region of interest identification engine 246, a topological feature extraction engine 248, a temporal feature trajectory extraction engine 250, a scale-space analysis engine 252, a peak detection and salient image selection engine 254, a medical imaging study summary graphical user interface generation engine 256, and a medical image viewer interface 258.

In response to invocation of the medical imaging study summarization engine 240, such as in response to receiving a request from a client computing device, e.g., client computing device 210, to provide medical imaging data about a specified medical imaging study to a user, the medical imaging study summarization engine 240 accesses a medical image storage system, e.g., one or more storage systems storing corpora 206, 220, to retrieve the corresponding medical imaging study identified in the request. For example, a lookup operation may be performed by the medical image storage system interface 242, based on information identified in the received request, to retrieve the corresponding medical imaging study. The lookup operation may comprise looking up a patient identifier, e.g., patient name or other designator of a unique identity of the patient, looking up a date/time of the medical imaging study, lookup up a medical imaging source system identifier, e.g., the medical imaging study was done by XYZ Imaging, simply looking up a specific identifier of the medical imaging study itself, i.e. a medical imaging study ID, or any other way to identify a specific medical imaging study that corresponds to the medical imaging study that the user wishes to view. As discussed previously, the medical imaging study comprises a time series of captured medical images of a patient's anatomy, obtained from medical imaging source equipment, computing systems, or the like, e.g., MRI, CT, X-ray, or the like systems, which may then be stored in a digital format in as one or more data structures in a medical image storage system, such as part of corpora 206, 220, for example.

Having retrieved the medical imaging study via the medical image storage system interface 242, the medical images in the medical imaging study are provided to the medical image segmentation engine 244 where each of the medical images in the medical imaging study are segmented using region segmentation based on the intensity of pixels that correspond to various tissue types. This results in a plurality of contours corresponding to different anatomical structures present in the medical image, some of which may be pertinent to the particular purpose for the request to view the medical imaging study, and others may not be pertinent to the particular purpose.

The segmented medical images are provided to the region of interest (ROI) identification engine 246 which determines which ROI to focus on in the segmented medical images based on the specified purpose of the request, if any is specified in the request. For example, as noted above, the request may specify that the user wishes to identify cardiac anomalies, pulmonary anomalies, etc. for the patient. Based on the identification of the purpose for the request, a corresponding region of interest is determined. This corresponding region of interest is associated with one or more atlas medical images that have the contours and corresponding labels for the anatomical structures in the region of interest. The one or more atlas medical images are matched to the medical images in the segmented medical images to match contours in the segmented medical images to contours in the atlases and thereby generate a representation of the segmented medical images in which only the anatomical structures corresponding to the region of interest are maintained.

The resulting modified data for the medical image in which the labeled anatomical structures for the region of interest are present are provided to the topological feature extraction engine 248 which operates on this data to extract topological features of the anatomical structures. Depending on the particular region of interest (ROI) selected, and the particular purpose for which the medical imaging study summary is being generated, different topological features may be extracted. In general, these topological features may include various measurements of the anatomical structures present within the region of interest, e.g., tissue width, thicknesses of walls of structures, distributions of sizes of the structures in the region of interest, dimensions of the shapes within the region of interest, or the like.

The extracted topological features are provided to the temporal feature trajectory extraction engine 250 which generates either a one dimensional or multi-dimensional temporal trajectory based on the topological changes in subsequent images in the time series of medical images in the medical imaging study. That is, the topological features, along each of the dimensions of topological features extracted, are plotted along a time scale to show how the anatomical structures in the region of interest change over time in the medical imaging study. This leads to the creation of curves along one or more dimensions.

The scale-space analysis engine 252 analyzes the temporal trajectory using a scale-space analysis algorithm, such as a linear (Gaussian) scale-space algorithm or the like, to automatically detect the proper scale for analysis of the trajectory. Having determined the proper scale for analysis of the trajectory, the peak detection and salient image selection engine 254 uses the automatically determined scale to identify peaks of the topological features in the curves of the temporal trajectory. These peaks indicate medical images in the medical imaging study where the topological features of the structures in the region of interest change significantly from one medical image to the next in the time series of medical images in the medical study. The peak detection and salient image selection engine 254 selects medical images corresponding to the peaks of the topological feature trajectory as the subset of salient medical images of the medical imaging study to be used in the medical imaging study summary.

The medical imaging study summary graphical user interface generation engine 256 uses the subset of salient images selected from the medical imaging study to generate a storyboard graphical user interface output as part of a summary of the medical imaging study. It should be appreciated that in some illustrative embodiments, this storyboard graphical user interface may be the primary portion of the graphical user interface that is output via a medical image viewer. In other illustrative embodiments, this storyboard graphical user interface may be one component of a graphical user interface while other components may present other information about the corresponding patient. For example, in embodiments in which the mechanisms of the illustrative embodiments operate in conjunction with, or are integrated with, a healthcare cognitive system, the other operations of the healthcare cognitive system, such as processing patient electronic medical records to extract information, may result in additional information that is presented in the graphical user interface along with the storyboard graphical user interface generated based on the selected subset of salient medical images. Moreover, it should be appreciated that a storyboard, i.e. a time ordered series of medical images, is only one possible way of outputting the subset of salient medical images and other ways of depicting the salient medical images selected from the medical imaging study may be utilized without departing from the spirit and scope of the present invention.

The generated graphical user interface comprising the output of the selected subset of salient medical images, e.g., the storyboard graphical user interface, may be output to a medical professional, medical imaging specialist, or other authorized user via the medical image viewer interface 258. The medical image viewer interface 258 may be an interface accessible by a user via a browser in some illustrative embodiments, such that the graphical user interface graphical data is generated by the medical image viewer interface 258 and simply rendered by the browser application at the client computing device, e.g., client computing device 210. Alternatively, the graphical user interface may be sent as data structures to the client computing device 210 which then renders the graphical user interface locally using a locally present medical imaging viewer application.

Thus, through this process of processing a medical imaging study, a summary of the medical imaging study is generated that comprises a much smaller set of medical images that are determined to be the salient medical images of the medical imaging study most pertinent to the purpose for which the review of the medical imaging study is being conducted. As a result, the human user viewing the summary needs to review a substantially smaller set of medical images than he or she would otherwise have to in order to gather the information they need to perform an evaluation of the patient's medical condition and/or determine treatment options for the patient based on such medical conditions. That is, the resulting summary is more usable by medical personnel and easier to browse, allowing the medical personnel to obtain a necessary information for providing decision support more quickly and efficiently.

As is evident from the above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. Thus, having been configured to perform these specific operations, the resulting configured computing or data processing systems are not generic computing or data processing systems simply performing generic computing operations or functions. To the contrary, the specifically configured computing devices or data processing systems are specific non-generic computing devices or data processing systems. As such, FIG. 3 is provided as an example of one type of data processing system in which aspects of the present invention may be implemented through specific configuration of the data processing system via the loading of software into memory and execution of that particular software on one or more processors of the data processing system to perform the described operations. Many other types of data processing systems may be likewise configured to specifically implement the mechanisms of the illustrative embodiments.

FIG. 3 is a block diagram of an example data processing system in which aspects of the illustrative embodiments are implemented. Data processing system 300 is an example of a computer, such as server 204A or client 210 in FIG. 2, for example, in which computer usable code or instructions implementing the processes for illustrative embodiments of the present invention are located. In one illustrative embodiment, FIG. 3 represents a server computing device, such as a server 304A, which implements a medical image study viewing computing system 200 augmented to include the additional mechanisms of the medical imaging study summarization engine 240 in accordance with one or more of the illustrative embodiments described above with regard.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340. HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System p® computer system, running the Advanced Interactive Executive) (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
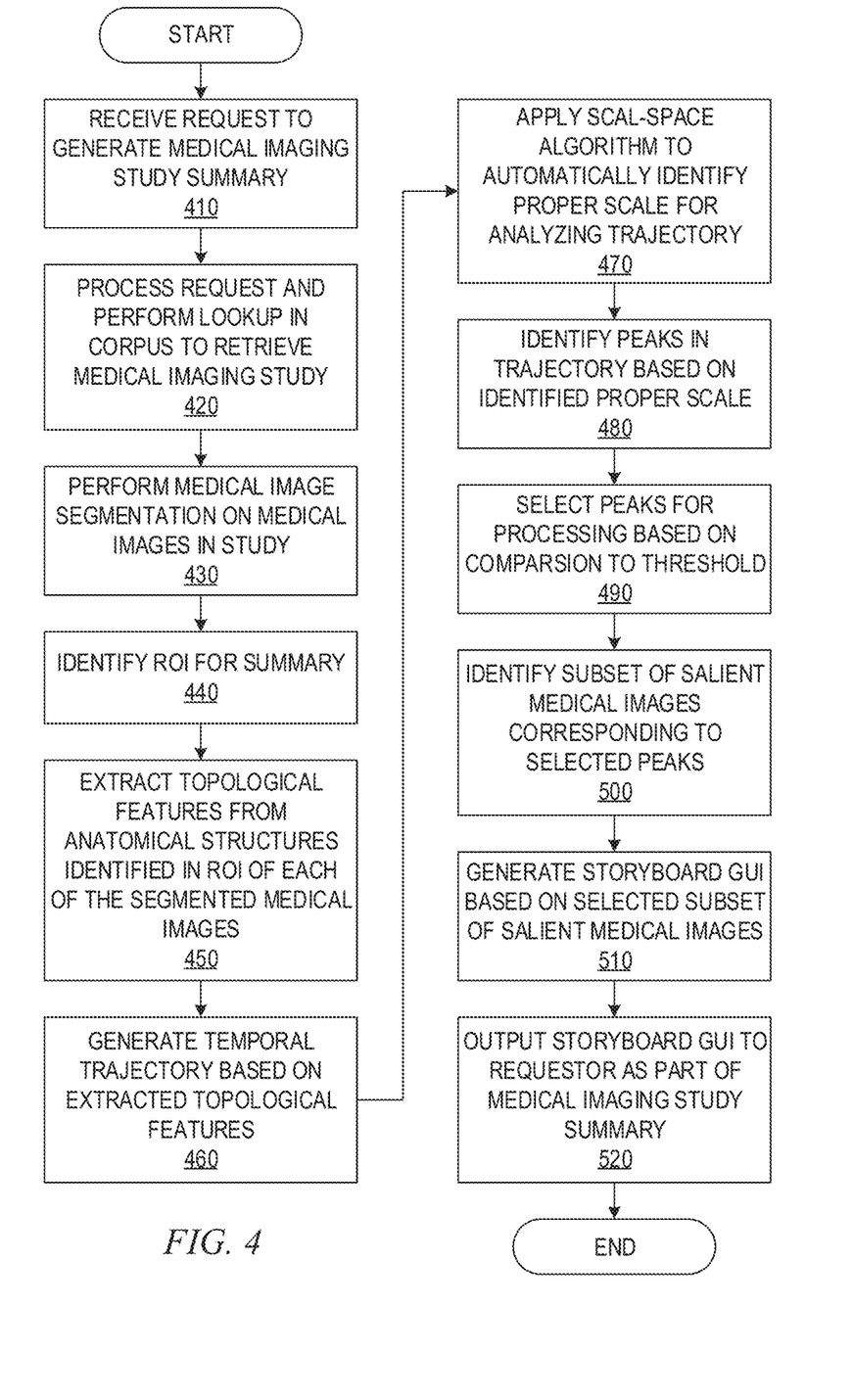
FIG. 4 is a flowchart outlining an example operation for generating a medical imaging study summary graphical user interface output in accordance with one illustrative embodiment.

FIG. 4 is a flowchart outlining an example operation for generating a medical imaging study summary graphical user interface output in accordance with one illustrative embodiment. As shown in FIG. 4, the operation starts by receiving a request to generate a medical imaging study summary for a particular identified medical imaging study (step 410). The request may specify the medical imaging study in a variety of different ways as discussed previously, and may specify one or more criteria for identifying a region of interest in medical images of the medical imaging study that are to be the focus of the summary generation. The request is processed and a lookup is performed in a corpus of medical imaging studies to identify the particular medical imaging study to be summarized (step 420).

The medical images in the medical imaging study are segmented, such as based on the intensity of pixels corresponding to different tissue types, for example, to generate segmented medical images (step 430). A region of interest (ROI) is identified for the summary based on the criteria specified in the request, if any (step 440). If no criteria are specified, then the entirety of the segmented medical images is utilized as the region of interest.

Topological features are extracted from anatomical structures identified in the ROI in each of the segmented medical images, or slices (step 450). The topological features are then used to generate a temporal trajectory that identifies changes in subsequent medical images in the time series of medical images of the medical imaging study (step 460). A scale-space analysis algorithm is applied to the temporal trajectory to determine the proper scale for analyzing the trajectory (step 470). The determined proper scale is then used to identify peaks in the trajectory (step 480). The determination of peaks may further involve comparing peak values to a threshold value that indicates peaks of interest, where only the peaks that are equal to or greater than the threshold are further processed for selection of salient medical images (step 490). This is an optional operation.

Based on the identified peaks of the topological feature trajectory, corresponding salient medical images from the medical imaging study that match the time point of the peaks are selected (step 500). The selected subset of medical images are then used to generate a storyboard graphical user interface showing a time progression of the subset of salient medical images (step 510). The storyboard graphical user interface is then output to the requestor as part of a medical imaging study summary graphical user interface via a medical imaging viewer interface or application (step 520) through which the user may browse and/or manipulate the depiction of the salient medical images in the medical imaging study graphical user interface. The operation then terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to configure the processor to implement a medical imaging study summary engine, the method comprising:
    receiving, by the medical imaging study summary engine, a medical imaging study data structure having data representing a plurality of medical images of a patient;
    generating, by the medical imaging study summary engine, a temporal trajectory data structure of at least a subset of the medical images in the plurality of medical images, wherein the temporal trajectory data structure specifies topological changes in temporally subsequent medical images in the plurality of medical images;
    selecting, by the medical imaging study summary engine, medical image data corresponding to selected medical images from the medical imaging study data structure based on the temporal trajectory data structure; and
    outputting, by the medical imaging study summary engine, the selected medical image data via a medical imaging study user interface at least by generating a storyboard representation of the medical imaging study based on the selected medical images.

2. The method of claim 1, wherein generating the temporal trajectory data structure comprises, for each medical image in the medical imaging study data structure:
    segmenting the medical image to identify anatomical structures present within the medical images;
    selecting a region of interest (ROI) in the medical image; and
    extracting topological features of the ROI, wherein the temporal trajectory is generated based on changes in the topological features of the ROI for temporally subsequent medical images.

3. The method of claim 2, wherein selecting medical image data from the medical imaging study data structure based on the temporal trajectory comprises analyzing the temporal trajectory data structure to identify salient portions of a temporal trajectory and selecting medical image data for the salient portions of the temporal trajectory.

4. The method of claim 2, wherein the ROI is selected based on a purpose of a medical imaging study summary specified in a user request input to the medical imaging study summary engine, and a correlation of the purpose of the medical imaging study summary with anatomical structures in the medical image data of the medical imaging study data structure.

5. The method of claim 4, wherein selecting the ROI further comprises comparing the medical image data of the medical imaging study data structure to previously labeled medical images corresponding to the purpose of the medical imaging study summary.

6. The method of claim 4, wherein the topological features of the ROI that are extracted are topological features specific to the particular purpose of the medical imaging study summary, and wherein the topological features are measurements of anatomical structures present within the region of interest.

7. The method of claim 2, wherein selecting the ROI comprises performing a multi-thresholding operation on an intensity histogram of the medical image data in the medical imaging study data structure and performing color connected component grouping on image characteristics of the medical image data to identify anatomical structures having similar characteristics.

8. The method of claim 2, wherein extracting topological features of the ROI comprises:
    extracting, from the ROI the first moment or area, second moments describing orientation, and a number of regions adjacent to another region;
    generating a histogram of a range of values for each of the extracted topological features;
    identifying peaks in the histogram to generate a multi-dimensional topological feature vector;
    computing the multi-dimensional topological feature vector for each successive medical image in the medical image data of the medical imaging study data structure to generate a time-varying multi-dimensional topological feature vector curve;
    performing a scale-space operation on the time varying multi-dimensional topological feature vector curve; and
    identifying peaks in the time varying multi-dimensional topological feature vector curve that are above an optimal level identified by the scale-space operation, wherein the optimal level specifies a level of smoothing and level of approximation error.

9. The method of claim 1, wherein selecting, by the medical imaging study summary engine, medical image data corresponding to selected medical images from the medical imaging study data structure based on a temporal trajectory data structure comprises selecting medical images from the medical imaging study data structure in which structures in the ROI of the selected medical images have characteristics that change above a predetermined level in a time series of medical images of the temporal trajectory data structure.

10. A computer program product comprising a non-transitory computer readable medium having a computer readable program stored therein, wherein the computer readable program, when executed on a computing device, causes the computing device to implement a medical imaging study summary engine that operates to:

receive a medical imaging study data structure having data representing a plurality of medical images of a patient;

generate a temporal trajectory data structure of at least a subset of the medical images in the plurality of medical images, wherein the temporal trajectory data structure specifies topological changes in temporally subsequent medical images in the plurality of medical images;

select medical image data corresponding to selected medical images from the medical imaging study data structure based on the temporal trajectory data structure; and output the selected medical image data via a medical imaging study user interface at least by generating a storyboard representation of the medical imaging study based on the selected medical images.

11. The computer program product of claim 10, wherein the computer readable program further causes the medical imaging study summary engine to generate the temporal trajectory data structure at least by, for each medical image in the medical imaging study data structure:

segmenting the medical image to identify anatomical structures present within the medical images;

selecting a region of interest (ROI) in the medical image; and extracting topological features of the ROI, wherein the temporal trajectory is generated based on changes in the topological features of the ROI for temporally subsequent medical images.

12. The computer program product of claim 11, wherein the computer readable program further causes the medical imaging study summary engine to select medical image data from the medical imaging study data structure based on the temporal trajectory at least by analyzing the temporal trajectory data structure to identify salient portions of a temporal trajectory and selecting medical image data for the salient portions of the temporal trajectory.

13. The computer program product of claim 11, wherein the ROI is selected based on a purpose of a medical imaging study summary specified in a user request input to the medical imaging study summary engine, and a correlation of the purpose of the medical imaging study summary with anatomical structures in the medical image data of the medical imaging study data structure.

14. The computer program product of claim 13, wherein the computer readable program further causes the medical imaging study summary engine to select the ROI further at least by comparing the medical image data of the medical imaging study data structure to previously labeled medical images corresponding to the purpose of the medical imaging study summary.

15. The computer program product of claim 13, wherein the topological features of the ROI that are extracted are topological features specific to the particular purpose of the medical imaging study summary, and wherein the topological features are measurements of anatomical structures present within the region of interest.

16. The computer program product of claim 11, wherein the computer readable program further causes the medical imaging study summary engine to select the ROI at least by performing a multi-thresholding operation on an intensity histogram of the medical image data in the medical imaging study data structure and performing color connected component grouping on image characteristics of the medical image data to identify anatomical structures having similar characteristics.

17. The computer program product of claim 11, wherein the computer readable program further causes the medical imaging study summary engine to extract topological features of the ROI at least by:

extracting, from the ROI the first moment or area, second moments describing orientation, and a number of regions adjacent to another region;

generating a histogram of a range of values for each of the extracted topological features;

identifying peaks in the histogram to generate a multi-dimensional topological feature vector;

computing the multi-dimensional topological feature vector for each successive medical image in the medical image data of the medical imaging study data structure to generate a time-varying multi-dimensional topological feature vector curve;

performing a scale-space operation on the time varying multi-dimensional topological feature vector curve; and identifying peaks in the time varying multi-dimensional topological feature vector curve that are above an optimal level identified by the scale-space operation, wherein the optimal level specifies a level of smoothing and level of approximation error.

18. The computer program product of claim 10, wherein the computer readable program further causes the medical imaging study summary engine to select medical image data corresponding to selected medical images from the medical imaging study data structure based on a temporal trajectory data structure at least by selecting medical images from the medical imaging study data structure in which structures in the ROI of the selected medical images have characteristics that change above a predetermined level in a time series of medical images of the temporal trajectory data structure.

19. An apparatus comprising:

a processor; and a memory coupled to the processor, wherein the memory comprises instructions which, when executed by the processor, cause the processor to implement a medical imaging study summary engine that operates to:

receive a medical imaging study data structure having data representing a plurality of medical images of a patient;

generate a temporal trajectory data structure of at least a subset of the medical images in the plurality of medical images, wherein the temporal trajectory data structure specifies topological changes in temporally subsequent medical images in the plurality of medical images;

select medical image data corresponding to selected medical images from the medical imaging study data structure based on the temporal trajectory data structure; and output the selected medical image data via a medical imaging study user interface at least by generating a storyboard representation of the medical imaging study based on the selected medical images.

* * * * *